US00PP18573P3

(12) United States Plant Patent
Yencho et al.

(10) Patent No.: US PP18,573 P3
(45) Date of Patent: Mar. 11, 2008

(54) ORNAMENTAL SWEETPOTATO PLANT NAMED 'SWEET CAROLINE SWEETHEART PURPLE'

(50) Latin Name: *Ipomoea batatas*
Varietal Denomination: Sweet Caroline Sweetheart Purple

(75) Inventors: George Craig Yencho, Raleigh, NC (US); Kenneth Pecota, Raleigh, NC (US); Charles Newell Hancock, Bear Creek, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 11/394,885

(22) Filed: Mar. 31, 2006

(65) Prior Publication Data

US 2007/0143893 P1 Jun. 21, 2007

Related U.S. Application Data

(60) Provisional application No. 60/752,486, filed on Dec. 21, 2005.

(51) Int. Cl.
*A01H 5/00* (2006.01)

(52) U.S. Cl. ..... Plt./258

(58) Field of Classification Search ..... Plt./258
See application file for complete search history.

(56) References Cited

U.S. PATENT DOCUMENTS

2007/0143893 P1 * 6/2007 Yencho et al. ..... Plt./258

* cited by examiner

*Primary Examiner*—Wendy C. Haas
*Assistant Examiner*—George Helmer
(74) *Attorney, Agent, or Firm*—Myers Bigel Sibley & Sajovec P.A.

(57) ABSTRACT

*Ipomoea batatas* 'Sweet Caroline Sweetheart Purple' is a compact to moderately-compact cultivar producing many shoots and having dense foliage. This cultivar is distinguishable from other cultivars by its small to medium-sized heart- to spade-shaped dark purple leaves. The plant has a good vigor, but is less vigorous than *Ipomoea batatas* 'Margarita' and 'Blackie' and unlike these cultivars, 'Sweet Caroline Sweetheart Purple' may be grown in containers with other species. The production of flowers by 'Sweet Caroline Sweetheart Purple' is relatively rare even under short day conditions.

2 Drawing Sheets

Latin name of the genus and species:

The Latin name of the novel, ornamental plant variety disclosed herein is *Ipomoea batatas* (L.) Lam.

Variety denomination:

The inventive cultivar of *Ipomoea batatas* disclosed herein has been given the varietal denomination 'Sweet Caroline Sweetheart Purple'.

BACKGROUND OF THE INVENTION

*Ipomoea* species are members of the morning glory family Convolvulaceae. *Ipomoea batatas,* the cultivated species, is commonly produced for consumption and referred to as the white or yellow sweetpotato and the orange yarm. The plants are typically fast growing, green vines possessing a wide variety of leaf shapes ranging from palmate and deeply lobed, to cordate or triangular shaped leaves with no lobes. Ornamental sweetpotatoes, which have been bred and selected for their unique foliage colors, leaf shapes and plant habits, typically do not produce large fleshy storage roots like the sweetpotato cultivated for consumption. In comparison, storage roots produced by ornamental sweetpotatoes are typically not as large because no selection has been exercised for yield, thus storage roots do not begin to swell until very late in the season. Further, the few storage roots that are formed by ornamental sweetpotatoes are typically not as attractive as those produced by the table stock types as they are generally cracked, very malformed, often mottled in skin and flesh color, and are not palatable.

Late in the growing season when day-lengths begin to shorten or when the plants are stressed, ornamental sweetpotato plants produce tubular flowers that are similar to morning glories, but most plantings are dominated by the appearance of the foliage. The plants are highly desirable due to their ability to grow under varied stress conditions, cover a large space, and last the entire growing season. Moreover, these plants have few insect or disease problems.

Until the release of the Sweet Caroline series of ornamental sweet potatoes (see below) there were six popular types of *Ipomoea batatas* ornamental sweetpotatoes being cultivated primarily for their annual, summer vines in landscaping applications. These six cultivars are: 'Blackie' (not patented), having purple foliage and lavender flowers; 'Terrace Lime' (not patented) and 'Margarita' (not patented; also known as 'Sulfur'), which have large brilliant chartreuse leaves and lavender blooms; 'Black Heart' (not patented; also known as 'Ace of Spades'), having heart-shaped leaves with burgundy purple color: 'Tricolor' (not patented; also known as 'Pink Frost'), a variegated plant having pale green, white, and pink-margined leaves; and 'Lady Fingers' (unpatented), which has medium green, dainty leaves divided into long, thin, fingerlike lobes that are complemented by burgundy stems and veins.

*Ipomoea batatas* 'Margarita' was recently released in the United States, and has become widely used as a landscape annual. However, it is not suitable for mixed containers as this variety exhibits a very vigorous growth and tends to out-complete other species. See Armitage. A. M. and J. M.

Garner, (2001) *Ipomoea batatas* 'Margarita'. HortScience 36:178. Another popular variety 'Blackie' is a vigorous purple-leaves clone, which is also unsuited to containerized gardens.

Therefore, to meet the current horticultural demand, it is desirable to produce new, more robust cultivars of ornamental sweetpotato with attractive foliage colors, leaf shapes, and plant architectures. In addition, it would be advantageous to develop cultivars of ornamental sweetpotato exhibiting a more compact growth, and which do not outcomplete other species in mixed containers.

*Ipomoea batatas* 'Sweet Caroline Light Green' (U.S. Plant Pat. No. PP 15,028, issued Jul. 20, 2004), 'Sweet Caroline Green' (U.S. Plant Pat. No. PP 15,056, issued Aug. 3, 2004), 'Sweet Caroline Bronze' (U.S. Plant Pat. No. PP 15,437, issued Dec. 21, 2004), 'Sweet Caroline Purple' (U.S. Plant Pat. No. PP 14,912, issued Jun. 15, 2004), and 'Sweet Caroline Red' (U.S. Plant Pat. No. PP 17,483 issued Mar. 13, 2007) are recently introduced cultivars developed at North Caroline State University that are characterized by compact growth habit, moderate to deeply lobed palmate leaves, and attractive foliage color.

The present invention relates to a new and distinct variety of *Ipomoea batatas* named 'Sweet Caroline Sweetheart Purple'. 'Sweet Caroline Sweetheart Purple' is a compact to moderately-compact, variety producing many shoots and having dense foliage. This variety is distinguishable from other varieties by its small to medium-sized heart- to spade-shaped dark purple leaves. The plant has a good vigor, but is less vigorous than 'Margarita' and 'Blackie' and, unlike these varieties, 'Sweet Caroline Sweetheart Purple' may be grown in containers with other species.

Lineage. The *Ipomoea batatas* 'Sweet Caroline Sweetheart Purple' cultivar (breeding designation NC1645-24NORN) is derived from seed of open pollinated NC308-1ORN obtained in, Raleigh, N.C. during October 2001 to April 2002.

NC308-1ORN resulted from a cross between the clone 'L84-74×BL-22' (female parent; unpatented) and the clone 'W021×BL-1' (male parent; unpatented). Seed from NC308-1ORN were planted in the Horticultural Greenhouses in Spring 2002. 'Sweet Caroline Sweetheart Purple' is very distinct based on leaf shape and plant architecture (Table 2). 'Sweet Caroline Sweetheart Purple' was derived from an open pollinated breeding line designated NC308-1ORN. NC308-1ORN is a well-branched, upright, moderately trailing plant with moderately to deeply-lobed purple leaves. In addition, NC308-1ORN flowers well and has long peduncles. The male parent is unknown. The single, individual plant now known as *Ipomoea batatas* 'Sweet Caroline Sweetheart Purple' was selected in August and September 2002 because of its combination of exceptional features and has been propagated asexually since that time.

Asexual Reproduction. Since its selection, *Ipomoea batatas* 'Sweet Caroline Sweetheart Purple' has been asexually reproduced at, Raleigh, N.C. predominantly by vegetative propagation of vine cuttings. Successively, there have been three cycles of vegetative propagation, one cycle of tissue culture micropropagation, and multiple vegetative propagation cycles to increase the plant population. Asexual reproduction of the new Ornamental Sweetpotato cultivar by cuttings has shown that the unique features of the new cultivar are stable and the plant reproduces true to type in successive generations of asexual reproduction.

SUMMARY OF THE INVENTION

*Ipomoea batatas* 'Sweet Caroline Sweetheart Purple' is a compact to moderately-compact cultivar producing many shoots and having dense foliage. This cultivar is distinguishable from other cultivars by its small to medium-sized heart- to spade-shaped dark purple leaves. The plant has a good vigor, but is less vigorous than *Ipomoea batatas* 'Margarita' and 'Blackie', and unlike these cultivars, 'Sweet Caroline Sweetheart Purple' may be grown in containers with other species. The production of flowers by 'Sweet Caroline Sweetheart Purple' is relatively rare even under short day conditions.

BRIEF DESCRIPTION OF THE DRAWINGS

The photographs in the drawings were made using conventional techniques and show the colors as true as reasonably possible by conventional photography. Colors in the photographs may differ slightly from the color values cited in the detailed botanical description, which accurately describe the colors of the new *Ipomoea batatas*.

DETAILED BOTANICAL DESCRIPTION

Figure 1:
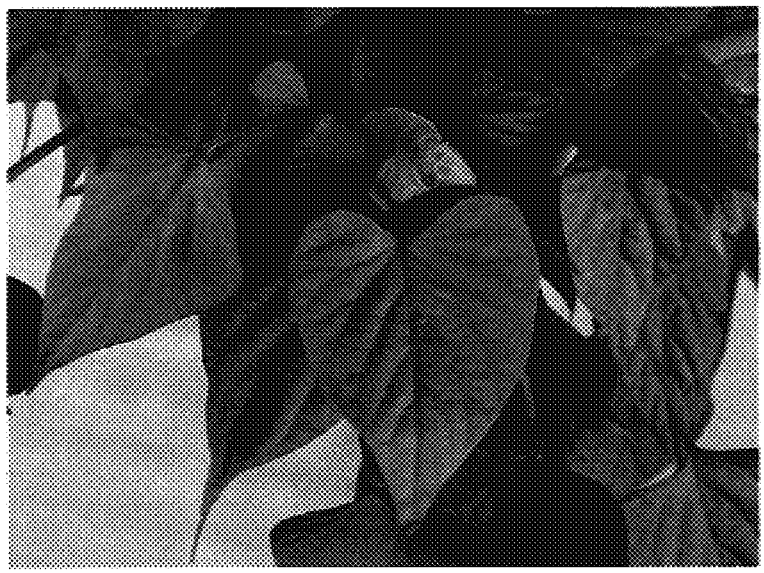
FIG. 1 is a color photograph showing both new and mature foliage produced by *Ipomoea batatas* 'Sweet Caroline Sweetheart Purple'. The plant shown in FIG. 1 is 11 weeks of age.
Figure 2:
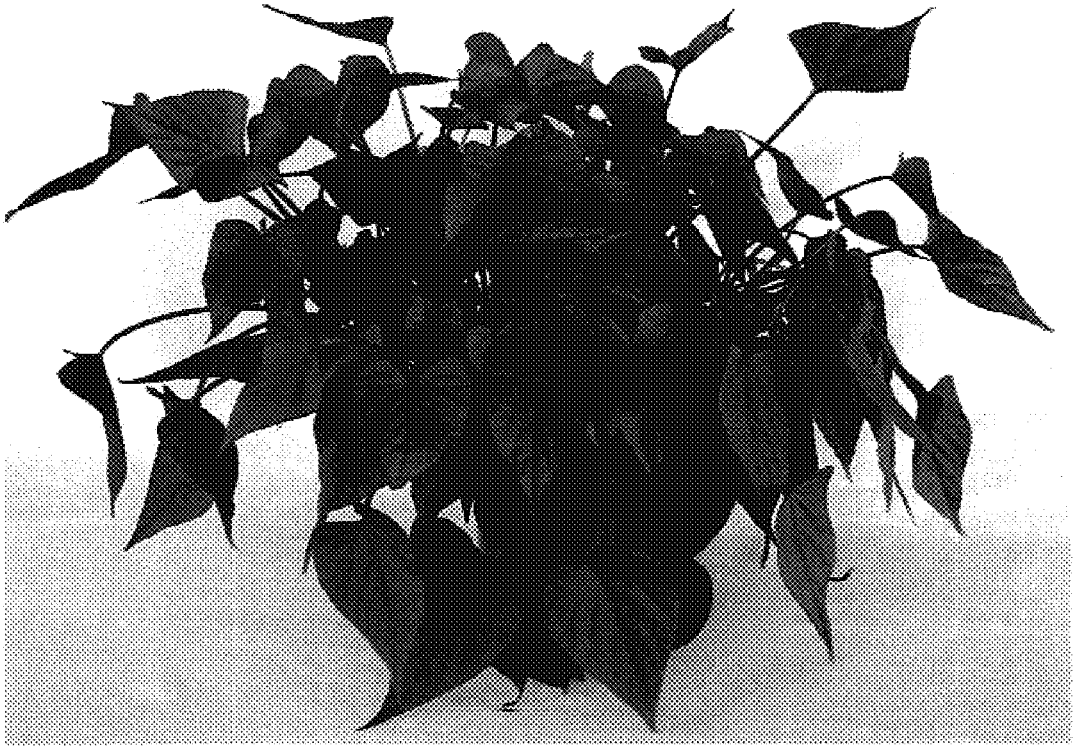
FIG. 2 is a color photograph of a typical plant of the *Ipomoea batatas* 'Sweet Caroline Sweetheart Purple'. The plant shown in FIG. 2 is 11 weeks of age.

The following is a detailed description of the botanical characteristics of the new and distinct cultivar of *Ipomoea batatas* plant known by the cultivar name *Ipomoea batatas* 'Sweet Caroline Sweetheart Purple'. All colors cited herein refer to The Royal Horticultural Society Chart (The Royal Horticultural Society, London, 1995 edition) designations except as indicated otherwise and where general terms of ordinary dictionary significance are used. Where dimensions, sizes, colors, and other characteristics are given, it is to be understood that such characteristics are approximations or averages set forth as accurately as practicable.

The descriptions reported herein are from 11-week-old specimens. *Ipomoea batatas* 'Sweet Caroline Sweetheart Purple' has not been observed under all possible environmental conditions; therefore, the phenotype may vary under different environmental conditions such as season, temperature, light intensity, day length, cultural conditions, and the like, without however any variance in the genotype.

Technical Description of the Variety.

Above-Ground Structure. Overall, the cultivar, *Ipomoea batatas* 'Sweet Caroline Sweetheart Purple', is a round compact mounding plant. Plant height is 25 cm and its area of spread is 44 cm. It is a moderately fast grower with good vigor.

Branching habitat. Very free branching with basal shoots. Adventitious roots develop at nodes and will root if in contact with soil.

Lateral shoots. The number of lateral shoots varies but averages around 14 with multiple short secondary shoots. Lateral branch length: ~20 cm. Diameter: 0.4 cm. Internode length: 1.5 cm. Stems are round, smooth and sturdy, without any pubescence. Shoots are initially upright but then fall outward, forming a dense canopy due to the many overlapping stems. Color: very dark purple (RHS 183A).

Petiole. Leaf petiole length is highly variable averaging 14 cm but up to 18 cm. Diameter: 0.35 cm. Texture: smooth. Color: 187A above and below. The long petioles allow the decorative heart-shaped leaves to arch up and outward resulting in a compact mounding plant.

Foliage. Leaves are alternate and tend to spiral around the stems. They are simple and heart-shaped (cordate) to triangular. The number of leaves per stem varies with length but an average stem has ~18 leaves. The leaf tip is acuminate and the base is cordate. Leaf margins are entire and the leaves are smooth and mat with no pubescence. Leaf length averages 11.5 cm and leaf width averages 8 cm. The venation pattern is palmate at the leaf base becoming arcuate toward the leaf tip. When the leaves emerge they are bright green but as they expand and mature, they develop anthocyanin pigment which looks bronze initially but turns violet to nearly black. Color: see Table 1.

TABLE 1

| Leaf Structure | Upper Surface | Lower Surface |
|---|---|---|
| Young Leaf | Bright green, RHS 146A | Bright green, RHS 146B |
| Mature Leaf | Dark purple, RHS N186A* | RHS 187A |
| Vein | 202A | 187A |

*The Royal Horticultural Society Colour Chart (The Royal Horticultural Society, London, 2001 edition)

Flowers. The production of flowers by 'Sweet Caroline Sweetheart Purple' is sparse to rare even under short day conditions. The precise photoperiod for flower induction is currently unknown. It may also flower sporadically throughout the season in response to a variety of stressful conditions (e.g., drought, nutrient stress, cloudy weather). It is noted that not only is flowering in this variety rare, but also, when flowers are produced, they are ephemeral (in most cases open only in the morning).

The inflorescence is generally a cyme in which the peduncle is divided into multiple axillary peduncles. Peduncles are purple (Color: 59A), averaging 72 mm long from mature leaf axils with an average diameter of 2 mm. Usually buds of the first, second, and third order are developed, but sometimes, single flowers are produced. Buds are yellow colored at tip (Color 150B to 150C) gradually changing to lavender at base, ovate, and around 19 mm in length and 4 mm in diameter 24 hours before opening.

The corolla is composed of five fused petals that form a funnel with a pentagonal limb. Corolla width: ~3.7 cm, corolla length: ~3.8 cm. The corolla is not fragrant. The limb and outer throat color are lavender and the inner throat color is purple. Inner limb color: 84B, Outer limb color: 84C, Inner throat color: 77A, Outer throat color: 84C. There are five sepals, with an average length of 10 mm and width of 3.2 mm. The sepals are elliptic with an acute apex and purple in color. Outer sepal color: 59A, Inner sepal color: 59C.

Each flower has one pistil with a white colored style (Color: 155A). The stigma is cream colored (Color: 157B) and averages about 2 mm wide and 16.7 mm long and has two segments. The stigma is exerted relative to the stamens. The ovary is yellow (Color: 1C) and superior with two locules that contain one or two ovules. Orange basal glands (Color: 17B) containing nectar are at the base of the ovary. There are five cream colored anthers (Color: 158C) that are approximately 3 mm long. Pollen (Color: 158C) is abundant. True seed are difficult to obtain, even with compatible crosses. There is some variation in flower size and color, depending on the environmental conditions. Descriptions are based on: CIP, AVRDC, IBPGR, 1991. Descriptors for Sweet Potato. Huaman, Z., editor. International board for Plant Genetic Resources, Rome, Italy.

Figure 3:
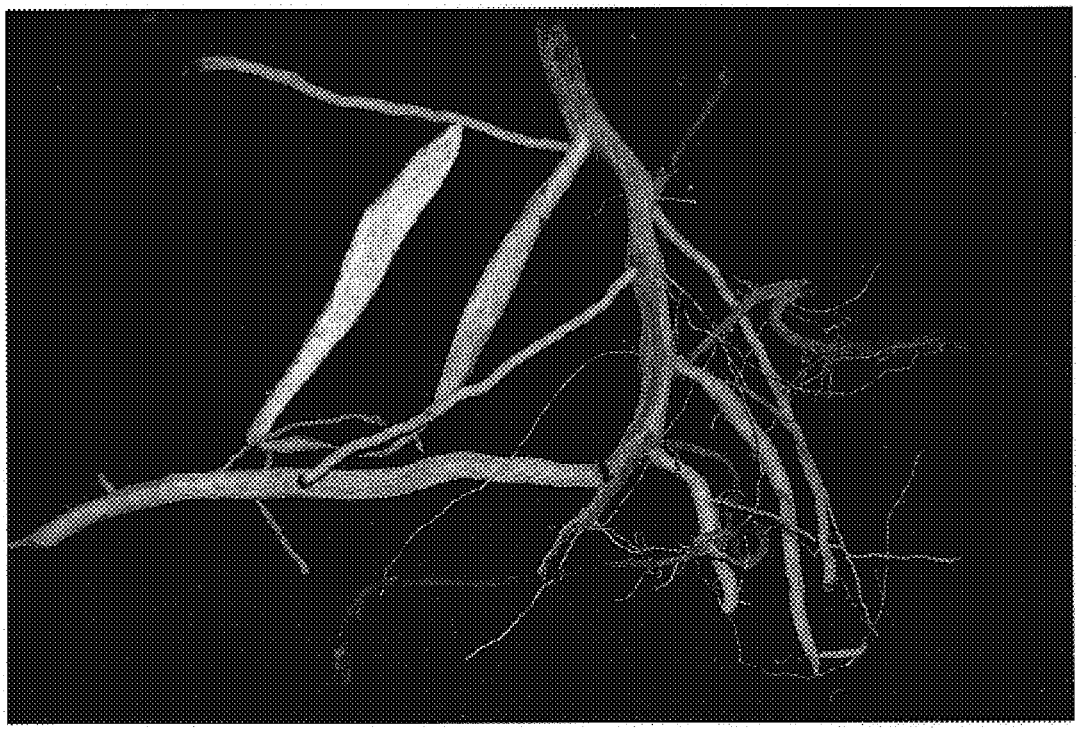
FIG. 3 is a color photograph showing typical storage roots produced by *Ipomoea batatas* 'Sweet Caroline Sweetheart Purple' 123 days after planting. Plants were planted as five-hill plots spaced 30.5 cm apart in the row at the Horticultural Crops Research Station, Clinton, N.C. USA.

Below-Ground structure. Plants form no, to very small, underground storage roots that are highly malformed and do not meet USDA Sweetpotato Storage Root Grade Standards (FIG. 3). Storage roots that do form typically possess cream colored skin (161C) with a cream colored flesh (160B).

Growth conditions. *Ipomoea batatas* 'Sweet Caroline Sweetheart Purple' has excellent vigor, a moderately fast growth rate, and is very adaptable to container culture. In locales with mild winter conditions. *Ipomoea batatas* 'Sweet Caroline Sweetheart Purple' will grow perennially; otherwise it is an annual plant. Similar to cultivated sweetpotatoes, wind or rain rarely causes much damage to 'Sweet Caroline Sweetheart Purple', but if damage does occur, the plants drops the damaged leaves and grows new shoots at nodes where the leaves were lost.

Disease or pest resistance. 'Sweet Caroline Sweetheart Purple' is susceptible to Sweetpotato Feathery Mottle Virus, white rust (caused by *Albugo ipomoeae-panduratae*) and damage by Japanese beetles.

Comparison with other *Ipomoea batatas* cultivars.

Comparison With Other *Ipomoea batatas* Cultivars. 'Sweet Caroline Sweetheart Purple' is very distinct based on leaf shape and plant architecture (Table 2). Of the six most common cultivars of ornamental sweetpotato, *Ipomoea batatas* 'Sweet Caroline Sweetheart Purple' is best compared with 'Sweet Caroline Purple' and 'Black Heart'. 'Sweet Caroline Purple' has purple, deeply lobed leaves, whereas, 'Sweet Caroline Sweetheart Purple' possesses heart- to spade-shaped leaves. 'Sweet Caroline Sweetheart Purple' exhibits a compact to moderately compact growth habit, while 'Sweet Caroline Purple' has a moderately compact plant habit and 'Black Heart' has a moderately trailing habit. 'Black Heart' has spade-shaped leaves that are bigger than those of 'Sweet Caroline Sweetheart Purple' and is moderately to poorly branched, compared to the well branched habit of 'Sweet Caroline Sweetheart Purple'. Both 'Sweet Caroline Sweetheart Purple' and 'Sweet Caroline Purple' are highly branched resulting in a more bunched and fuller appearance, which is more suitable for containerized propagation, as compared to 'Black Heart'.

TABLE 2

| Characteristic | New Variety 'Sweet Caroline Sweetheart Purple' | Comparison 1 'Sweet Caroline Purple' | Comparison 2 'Black Heart' |
|---|---|---|---|
| Plant Habit | Compact to Moderately Compact | Moderately Compact | Moderately Trailing |
| Branching | Highly Branched | Highly Branched | Poorly to Moderately Branched |
| Foliage Color | Purple | Dark Purple | Purple |
| Leaf Size | Small to Moderate | Moderate | Moderate to Large |
| Leaf Shape | Heart- to spade-shaped | Deeply Lobed | Heart- to spade-shaped |

What is claimed is:

1. A new and distinct cultivar of *Ipomoea batatas* plant named 'Sweet Caroline Sweetheart Purple', substantially as illustrated and described herein.

* * * * *